United States Patent
Dudovich et al.

(10) Patent No.: US 9,970,891 B2
(45) Date of Patent: May 15, 2018

(54) SYSTEM AND METHOD FOR PHASE RETRIEVAL IN LENSLESS IMAGING

(71) Applicant: YEDA RESEARCH AND DEVELOPMENT CO. LTD., Rehovot (IL)

(72) Inventors: Nirit Dudovich, Rehovot (IL); Oren Raz, Rehovot (IL); Boaz Nadler, Rehovot (IL); Dan Oron, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 65 days.

(21) Appl. No.: 15/033,911

(22) PCT Filed: Nov. 4, 2014

(86) PCT No.: PCT/IL2014/050956
§ 371 (c)(1),
(2) Date: May 3, 2016

(87) PCT Pub. No.: WO2015/063779
PCT Pub. Date: May 7, 2015

(65) Prior Publication Data
US 2016/0266057 A1  Sep. 15, 2016

Related U.S. Application Data

(60) Provisional application No. 61/899,380, filed on Nov. 4, 2013.

(51) Int. Cl.
*G06K 9/00* (2006.01)
*G01N 23/205* (2018.01)
(Continued)

(52) U.S. Cl.
CPC ..... *G01N 23/2055* (2013.01); *G02B 21/0056* (2013.01); *G02B 21/367* (2013.01);
(Continued)

(58) Field of Classification Search
None
See application file for complete search history.

(56) References Cited

U.S. PATENT DOCUMENTS

| 7,643,400 B1* | 1/2010 | Iazikov | G11B 7/24038 369/109.01 |
| 2007/0242868 A1* | 10/2007 | Stanton | G01N 23/046 382/131 |

(Continued)

OTHER PUBLICATIONS

Candes et al. "Phase retrieval via matrix completion" arXiv:1109. 0573v2 (2011) (SIAM review. May 8, 2015;57(2):225-51).
(Continued)

*Primary Examiner* — Hadi Akhavannik
(74) *Attorney, Agent, or Firm* — Mark S. Cohen; Pearl Cohen Zedek Latzer Baratz LLP

(57) ABSTRACT

A method and system for use in reconstruction and retrieval of phase information associated with a two-dimensional diffractive response are presented. The method comprising: providing (75) input data indicative of one or more diffractive patterns corresponding to diffractive responses from one or more objects (50). Dividing (130) said input data into a plurality of one-dimensional slices and determining (140) one-dimensional phase data for at least some of said one-dimensional slices. Tailoring (150) the reconstructed phase data of said one-dimensional slices to form a two-dimensional phase solution. The two-dimensional phase solution is defined by phase shifts of said reconstructed one-dimensional phase data of said one-dimensional slices. The two-dimensional phase solution thus enables obtaining two-dimensional reconstructed phase data suitable for reconstruction of image data (250).

14 Claims, 12 Drawing Sheets

(51) Int. Cl.
  G03H 1/08    (2006.01)
  G03H 1/12    (2006.01)
  G02B 21/00   (2006.01)
  G02B 21/36   (2006.01)
  G06T 7/30    (2017.01)
  G01N 23/20   (2018.01)
  G03H 5/00    (2006.01)
  G03H 1/04    (2006.01)

(52) U.S. Cl.
  CPC ......... *G03H 1/0443* (2013.01); *G03H 1/0866* (2013.01); *G03H 1/12* (2013.01); *G06T 7/30* (2017.01); *G01N 23/20* (2013.01); *G03H 5/00* (2013.01); *G03H 2001/045* (2013.01); *G03H 2001/0447* (2013.01); *G03H 2001/0454* (2013.01); *G03H 2222/42* (2013.01)

(56) References Cited

U.S. PATENT DOCUMENTS

| | | | |
|---|---|---|---|
| 2008/0159642 A1 | 7/2008 | Lyuboshenko | |
| 2009/0316141 A1* | 12/2009 | Feldkhun | G01N 21/6458 356/217 |
| 2011/0085176 A1* | 4/2011 | Cramer | G03F 7/70625 356/601 |
| 2012/0257197 A1* | 10/2012 | Feldkhun | G01N 21/4795 356/301 |

OTHER PUBLICATIONS

Chapman et al. "Femtosecond X-ray protein nanocrystallography" Nature. Feb. 3, 2011;470(7332)73-7.

Chapman et al. "Coherent lensless X-ray imaging" Nature Photonics. Dec. 1, 2010;4(12):833-9.

Faulkner et al. "Movable aperture lensless transmission microscopy: a novel phase retrieval algorithm" Physical review letters. Jul. 9, 2004;93(2):023903.

Jiang et al. "Quantitative 3D imaging of whole, unstained cells by using X-ray diffraction microscopy" Proceedings of the National Academy of Sciences. Jun. 22, 2010;107(25):11234-9.

Marchesini S. "Invited article: A unified evaluation of iterative projection algorithms for phase retrieval" Review of scientific instruments. Jan. 2007; 8(1):011301.

Miao et al. "Extending the methodology of X-ray crystallography to allow imaging of micrometre-sized non-crystalline specimens" Nature. Jul. 22, 1999:400(6742):342-4.

Miao et al. "Quantitative image reconstruction of GaN quantum dots from oversampled diffraction intensities alone" Physical review letters. Aug. 17, 2005;95(8):085503.

Neice A. "Methods and limitations of subwavelength imaging" Advances in imaging and electron physics. Dec. 31, 2010;163:117-40.

Osherovich et al. "Phase retrieval combined with digital holography" arXiv preprint arXiv:1203.0853. Mar. 5, 2012.

Raz et al. "Vectorial phase retrieval of 1-D signals" IEEE Trans. Signal Processing. Apr. 1, 2013;61(7)1632-43.

Raz et al. "Direct phase retrieval in double blind Fourier holography" Optics express. Oct. 20, 2014;22(21):24935-50.

Raz et al. "Vectorial phase retrieval for linear characterization of attosecond pulses" Physical review letters. Sep. 19, 2011;107(13):133902.

Sandberg et al. "Lensless diffractive imaging using tabletop coherent high-harmonic soft-x-ray beams" Physical review letters. Aug. 29, 2007;99(9):098103.

Seibert et al. "Single mimivirus particles intercepted and imaged with an X-ray laser" Nature. Feb. 3, 2011;470(7332):78-81.

Waldspurger et al. "Phase recovery, maxcut and complex semidefinite programming" Mathematical Programming. arXiv.org/1206.0102 (2012) (Feb. 1, 2015;149(1-2):47-81).

* cited by examiner

SYSTEM AND METHOD FOR PHASE RETRIEVAL IN LENSLESS IMAGING

CROSS-REFERENCE TO RELATED APPLICATIONS

This application is a National Phase Application of PCT International Application No. PCT/IL2014/050956, International Filing Date Nov. 4, 2014, claiming priority of US Provisional Patent Application No. 61/899,380, filed Nov. 4, 2013, which are hereby incorporated by reference.

TECHNOLOGICAL FIELD

The present invention is in the field of imaging and image reconstruction, and is particularly useful for phase reconstruction associated with lensless imaging techniques.

REFERENCES

References considered to be relevant as background to the presently disclosed subject matter are listed below:
[1] Neice, A. Chapter 3—methods and limitations of subwavelength imaging. vol. 163 of Advances in Imaging and Electron Physics, 117-140 (Elsevier, 2010).
[2] N. Chapman, H. et al. Femtosecond x-ray protein nanocrystallography. Nature 470, 73-77 (2011).
[3] Seibert, M. M. et al. Single mimivirus particles intercepted and imaged with an x-ray laser. Nature 470, 78-81 (2011).
[4] Miao, J., Charalambous, P., Kirz, J. & Sayre, D. Extending the methodology of x-ray crystallography to allow imaging of micrometer-sized non-crystalline specimens. Nature 400, 342-344 (1999).
[5] Jianga, H. et al. Quantitative 3d imaging of whole, unstained cells by using x-ray diffraction microscopy. PNAS 107, 11234-11239 (2010).
[6] Chapman, H. N. & Nugent, K. A. Coherent lensless x-ray imaging. Nature Photonics 4, 833-839 (2010).
[7] Marchesini, S. A unified evaluation of iterative projection algorithms for phase retrieval. Review of Scientific Instruments/Volume 78/Issue 1 78, 011301-1:10 (2007).
[8] Faulkner, H. M. L. & Rodenburg, J. M. Movable aperture lensless transmission microscopy: A novel phase retrieval algorithm. Phys. Rev. Lett. 93, 023903 (2004).
[9] Candes, E., Eldar, Y., Strohmer, T. & V., V. Phase retrieval via matrix completion. arXiv:1109.0573v2 (2011).
[10] Waldspurger, I., D'Aspermont, A. & Mallat, S. Phase recovery, maxcut and complex semidefinite programming arXiv.org/1206.0102 (2012).
[11] Raz, O. et al. Vectorial phase retrieval for linear characterization of attosecond pulses. Phys. Rev. Lett. 107, 133902 (2011).
[12] Raz, O., Nadler, B. & Dudovich, N Vectorial phase retrieval for 1-d signals. IEEE Trans. Sig. Proc. (2013).
[13] Miao, J. et al. Quantitative image reconstruction of GaN quantum dots from oversampled diffraction intensities alone. Phys. Rev. Lett. 95, 085503 (2005).

Acknowledgement of the above references herein is not to be inferred as meaning that these are in any way relevant to the patentability of the presently disclosed subject matter.

BACKGROUND

High resolution imaging and microscopy revolutionized various fields of science and technology. Over the past century extensive efforts have been directed towards enhancing imaging resolution as well as enabling imaging of objects of smaller dimensions. The main limitation in resolving mini-scale structures is the diffraction limit, dictated by the optical wavelength.

A significant advance in resolving nanoscale structures was offered with the recent development of new laser sources such as the free electron laser (FEL) [2, 3], which provide coherent radiation in the x-ray regime enabling a use of shorter wavelengths. An additional important advance was the realization that crystallographic methods can be applied to non periodic objects. This approach, leading to techniques known as Coherent Diffractive Imaging (CDI) [4] or lensless imaging, has already been successfully used for imaging a variety of objects, from a yeast cell [5] through nano-crystals [3] and even a single virus [2].

Lensless imaging techniques enable indirect observation of objects (e.g. molecular structure) with high resolution by measuring intensity of diffraction patterns generated by scattering of coherent light from the objects. As known, light diffracted from an object forms a diffraction pattern indicative of a Fourier transform of the object. Reconstruction of an image of the object requires retrieving the phase of the diffraction pattern and calculating an inverse Fourier transform. However, retrieval of the phase data from intensity measurements is not a trivial task. This problem is generally denoted as the non-crystallographic phase problem. Various techniques of phase retrieval from intensity measurements have been subject of intensive studies over the past decades and are still some of the major challenges in lensless imaging techniques.

Generally, most objects to be imaged have a finite extent, usually termed the "compact support" of the object. Mathematically, this is the region where the function has non-zero value. It has been shown that for such finite objects, the two dimensional phase retrieval problem has a unique solution up to trivial ambiguities (linear phase and conjugation, generally corresponding to lateral shifts and/or reflections). In practice however, retrieving the phase based on intensity measurements is still a major challenge.

Over the past decades numerous approaches were proposed to solve the phase retrieval problem. The currently available techniques are divided based on a natural tradeoff between experimental complexity and computational reconstruction efficiency. On one end, simple and direct measurements of the diffracted intensity require intensive and iterative computational phase retrieval [6, 7]. On the other, multiple measurements, with increased experimental complexity enable to reduce the computational complexity of the phase retrieval problem.

In general, and even under noise free measurements, the available iterative phase retrieval approaches suffer from several limitations. The iterative algorithms do not always converge, and even when the calculation converges to a certain solution, corresponding to a local minimum of some optimization functional, there is no assurance that this solution is the correct one. Additionally, there is no clear and robust technique to evaluate the effects of noise or to provide exact estimation of the compact support thereby providing a measure for an error in the calculated solution. These difficulties have been addressed by recent approaches introducing new constraints and thus requiring additional measurements. One example is the Ptychographical Iterative Engine (PIE) [8], in which the object is scanned with a small known aperture, keeping an overlap between the inspection regions of every two positions of the aperture.

Additional recent approaches [9, 10] utilize structured illuminations of the object to be observed, in order to reduce the phase retrieval problem to a convex one. Although these techniques are mathematically promising, they raise various experimental difficulties limiting their efficiency. Moreover, these methods are highly computationally demanding and thus are limited to small images.

Recently, a novel technique was introduced by the inventors of the present invention for 1D Vectorial Phase Retrieval (VPR) [11, 12]. Generally, the VPR technique is useful for phase retrieval in problems where the signal of interest has a vectorial, or vectorial-like, nature. Examples of such vectorial like signal include signals having polarization or spin states. According to this technique, if the two components of the signal (for example x and y polarization components) are independent, and the signal has a certain (possibly unknown) support, then the 1D VPR technique provides the unique solution. Additionally, the VPR technique offers a significant advantage by allowing to solve the phase problem with a set of linear equations, making it both scalable and robust to noise.

GENERAL DESCRIPTION

There is a need in the art for a novel technique enabling efficient reconstruction of image data from associated diffraction patterns. The technique of the present invention provides relatively simple phase reconstruction capable of reconstructing image data based on two-dimensional diffractive patterns. Generally the technique of the present invention is suitable for use with lensless imaging techniques to provide direct, robust and efficient image data while requiring reduced computational and experimental complexity. As described above, the phase retrieval problem deals with the need to obtain data about the phase of a signal being measured. However, as the intensity measurement does not provide phase data, the actual reconstruction of the phase may not be simple.

The present invention provides a technique for use in reconstructing phase information based on two-dimensional diffractive patterns, generally associated with collected diffractive patterns such as in Coherent Diffractive Imaging (CDI), and thus enables retrieval of corresponding image data. Coherent Diffractive Imaging, as well as lens-less imaging, is techniques for imaging of objects by collecting data about optical radiation (or any wave or wave-like radiation) scattered from an object. As well known in the art, at far field distances, the diffractive pattern is indicative of Fourier transform of the object, and thus, an inverse Fourier transform can be calculated to obtain the image of the object. It should however be noted, and as indicated above, that in order to calculate the inverse Fourier transform to obtain accurate and meaningful result, the phase data of the collected diffractive pattern has to be reconstructed.

The technique of the present invention utilizes a conceptually different approach than the known two-dimensional phase reconstruction techniques, and enables a robust and efficient phase reconstruction while demanding relatively simple computation complexity. According to the present invention, the restriction of a compact support, is combined with the interference of the diffraction patterns from different parts of the imaged object, or between several imaged objects, convert the phase reconstruction problem into a linear set of equations. This allows fast and simple calculation of the phase information. According to some embodiments of the present invention, the two-dimensional phase problem is converted into a vectorial phase reconstruction problem. This allows separation of the two-dimensional data into a set of one-dimensional vectors and reconstructing the phase for the one-dimensional problems. This technique is based on the inventors' understanding that the use of vectorial signals may provide the desired information to obtain a simple solution for a one-dimensional phase problem. This Vectorial Phase Retrieval (VPR) technique enables to resolve the phase information of one-dimensional intensity signals while requiring only linear measurements and with relatively low computational complexity. It should be noted that generally the technique of the present invention allows for reconstruction of phase information based on one or more diffractive patterns of two or more objects or based on two or more diffractive patterns of one or more objects.

Thus, the technique of the present invention enables reconstruction of phase data from two-dimensional intensity measurements, by slicing the 2D measurement data into a plurality of 1D data pieces, solving the phase reconstruction problem for each of the 1D data pieces, and combining the plurality of 1D phase solutions to provide a unique solution for the 2D phase reconstruction. To this end, the technique of the present invention generally requires input data indicative of one or more diffractive measurements of one or more objects to be inspected. The diffractive measurements are typically obtained by Coherent Diffractive Imaging (CDI) utilizing coherent illumination of a certain wavelength range (e.g. certain wavelength range in the UV or X-ray regime).

For example, the input data is indicative of at least three diffractive measurements of a sample, which comprise two independent measurements of a sample (or two measurements of separate but similar samples), and an additional measurement corresponding to interference between the first two measurements.

For example, according to some embodiments, the at least three diffractive measurements comprise CDI measurement data of a first illumination channel, a second illumination channel and additional CDI measurement data utilizing both first and second illumination channels. The first and second illumination channels may be based on first and second light sources, a single light source selectively illuminating first and second parts of the sample through selectively located slits etc.

According to some other embodiments, the input data may be indicative of a diffractive pattern generated by radiation scattering from two or more well separated objects, i.e. two or more objects located at a distance larger than the size of the objects. The Input diffractive data may be preprocess to determine auto- and cross-correlation patterns associates with diffractive response of the two or more objects, thereby providing data about diffractive response for each of said two or more objects and an interference relation between them.

The technique of the invention comprises processing of the input data to identify phase information and thereby enabling reconstruction of image data indicative of the sample. The processing comprises separating the 2D input data into a set of 1D vectors; reconstructing phase information for each of the set of 1D vectors; and combining the set of reconstructed 1D phase information into a two-dimensional phase data. The resulting 2D phase data may then be output for storage or further calculation, and/or it may be used to calculate inverse Fourier transform to thereby obtain image data associated with the inspected sample.

According to some embodiments of the present invention, the phase reconstruction technique relays on a set of measurements of a single object taken through different apertures and/or separate measurements of an object and a duplicated thereof. According to some other embodiments, the technique utilizes a measured diffractive pattern generated by wave scattering from two or more objects in a single-shot measurement.

Thus, according to one broad aspect, the present invention provides a method for use in reconstruction of phase information associated with a two-dimensional diffractive response of one or more objects. The method comprising: providing input data indicative of one or more diffractive patterns corresponding to diffractive responses from said one or more objects; dividing said input data into a plurality of one-dimensional slices; determining one-dimensional phase data for at least some of said one-dimensional slices; tailoring the reconstructed phase data of said one-dimensional slices to thereby form a two-dimensional phase solution defined by phase shifts of said reconstructed one-dimensional phase data of said one-dimensional slices. Said two-dimensional phase solution enables to obtain two-dimensional reconstructed phase data suitable for reconstruction of image data.

The input data may comprise at least two independent intensity diffractive patterns associated with diffractive response of the one or more objects.

According to some embodiments of the invention, said one or more diffractive patterns comprises a diffractive pattern of two or more objects, the method further comprising generating said input data based on said diffractive pattern, said generating comprises determining cross-correlation and auto-correlation relations between said two or more objects from said diffractive pattern to thereby determine intensity pattern of said objects and interference relations between said two or more object.

According to some embodiments of the invention, the input data comprises at least three diffractive patterns associated with diffractive response of the one or more objects to at least three illumination channels. Said at least three diffractive patterns may comprise at least two independent intensity diffractive patterns associated with diffractive response of the object. Additionally, the at least three diffractive patterns comprise data indicative of at least: a first diffractive pattern generated by a first coherent illumination; a second diffractive pattern generated by a second coherent illumination; and a third diffractive pattern generated by a combination of the first and second coherent illuminations.

Said determining reconstructed one-dimensional phase data for said plurality of one-dimensional slices may comprise utilizing a cross term between said at least three diffractive patterns. Said cross-term may be indicative of a relative phase difference between the first and second diffractive patterns.

According to some embodiments, said determining the one-dimensional phase data for each of the plurality of one-dimensional slices comprises utilizing one-dimensional vectorial phase retrieval (VPR) technique.

According to one other broad aspect of the present invention there is provided a method for use in reconstruction of phase data associated with a two-dimensional diffractive response of an object. The method comprising: providing input data comprising data indicative at least three diffractive patterns corresponding respectively to diffractive response from said object obtained by a first coherent illumination, a second coherent illumination and a combined illumination being an interference of said first and second coherent illuminations; dividing each of said at least three diffractive patterns into plurality of one-dimensional slices to thereby form plurality of sets of matching slices of said at least three diffractive patterns; processing each set of matching slices to determine a reconstructed one-dimensional phase data thereof; tailoring the reconstructed one-dimensional phase data of said plurality of sets of matching slices to thereby reconstruct a two-dimensional phase data associated with said diffractive response from said object, said tailoring of the reconstructed one-dimensional phase data comprises determining phase shifts of said one-dimensional slices to provide said two-dimensional reconstructed phase data suitable for reconstruction of image data of said object.

According to yet another broad aspect of the present invention there is provided a method for use in reconstruction of phase data associated with a two-dimensional diffractive response of two or more objects. The method comprising: providing a single-shot diffractive pattern of said two or more objects; determining from said single-shot diffractive pattern, auto-correlation of the two or more objects and cross-correlation between them. Identifying intensity diffractive patterns of each of said two or more objects and interference relations between them based on the auto- and cross-correlation information; dividing each of said intensity diffractive patterns of said two or more objects and said interference relations between them into plurality of one-dimensional slices to thereby form plurality of sets of matching slices thereof; processing each set of matching slices to determine a reconstructed one-dimensional phase data for said slices; and tailoring the reconstructed one-dimensional phase data of said plurality of sets of matching slices to thereby reconstruct a two-dimensional phase data associated with said diffractive response from said two or more objects, said tailoring of the reconstructed one-dimensional phase data comprises determining phase shifts of said one-dimensional slices to provide said two-dimensional reconstructed phase data suitable for reconstruction of image data of said two or more objects.

It should be noted that the technique of the invention as described herein may be implemented as a software product. The software product may generally be embedded on a computer readable medium and carrying computer readable code comprising instructions such that when operated on a computer system configured to execute the method as described above.

According to yet another broad aspect of the invention there is provided a program storage device readable by machine, tangibly embodying a program of instructions executable by the machine to perform a method for use in reconstruction of phase information associated with a two-dimensional diffractive response of an object. The method comprising: providing input data indicative of one or more diffractive patterns corresponding to one or more diffractive response from said object; dividing said input data into a plurality of one-dimensional slices; determining reconstructed one-dimensional phase data for said plurality of one-dimensional slices; tailoring the reconstructed phase data of said plurality of one-dimensional slices to thereby form a two-dimensional phase solution determining phase shifts of said reconstructed one-dimensional phase data of said one-dimensional slices to provide two-dimensional reconstructed phase data suitable for reconstruction of image data.

According yet another broad aspect, the present invention provides a system for use in phase reconstruction. The system comprising a processing utility configured for processing input data being indicative of one or more two-dimensional diffractive patterns associated with diffractive response from one or more objects, and to determine reconstructed phase data based on said input data; the processing utility comprises:

a vector generating module configured to receive data indicative of said one or more and to generate a corresponding plurality of sets of one-dimensional vectors respectively corresponding to plurality of slices of said one or more two-dimensional diffractive patterns;

a one-dimensional phase reconstruction module configured to receive said sets of one-dimensional vectors, and to determine reconstructed one-dimensional phase data associated with said sets of one-dimensional vectors; and a two-dimensional phase tailoring module configured to receive data indicative plurality of reconstructed one-dimensional phase data from said one-dimensional phase reconstruction module and to generate a corresponding two-dimensional phase data indicative of reconstructed phase information associated with said input data.

According to some embodiments, the processing utility may be configured and operable for reconstruction of phase information based on input data, said input data comprises at least three diffractive patterns associated with diffractive response of the one or more objects. The at least three diffractive patterns may comprise at least first and second diffractive patterns, and at least a third diffractive patent being indicative of interference relation between said first and second diffractive patterns.

The processing utility may comprise a pre-processing module configured and operable to receive and process said input data to generate data indicative of a relative phase difference between at least two diffractive patterns of said one or more two-dimensional diffractive patterns.

According to some other embodiments of the invention the processing utility may comprise a pre-processing module configured and operable to receive and process data indicative of at least one diffractive pattern associated with a diffraction response of two or more objects. The pre-processing module being configured to determine input data based on said data indicative of at least one diffractive pattern, said input data comprising diffraction pattern of each of said at least two objects and an interference relation between them.

According to yet another broad aspect, the present invention provides a system for lens-less imaging. The system comprising: at least a first and second illumination channels for illuminating an object to be inspected, a detector unit comprising a pixel array for detecting scattered radiation from the object, and a control unit configured and operable for receiving data indicative of detected scattered radiation from said detector unit and processing said data to determine reconstructed image data of said object; said control unit being configured and operable for receiving input data comprising one or more two-dimensional diffractive patterns indicative of scattered light caused by the first and second illumination channels and for processing said input data to reconstruct image data indicative of the object to be inspected; said processing comprising: slicing said one or more two-dimensional diffractive patterns into plurality of one-dimensional slices to thereby form plurality of sets of matching slices of said one or more two-dimensional diffractive patterns; processing each set of matching slices to determine a reconstructed one-dimensional phase data thereof; tailoring the reconstructed one-dimensional phase data of said plurality of sets of matching slices to thereby reconstruct a two-dimensional phase data associated with said diffractive response from said object, said tailoring of the reconstructed one-dimensional phase data comprises determining phase shifts of said one-dimensional slices to provide said two-dimensional reconstructed phase data suitable for reconstruction of image data of said object; and determining an inverse Fourier transform based on the two-dimensional reconstructed phase data and said detected diffractive patterns to thereby reconstruct image data of the object. The control unit may be configured and operable to collect input data comprising first second and third diffractive patterns respectively associated with the first, second illumination channels and interference thereof.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 7A shows the two object being imaged; FIG. 7B shows a diffractive pattern resulting from lensless imaging of the objects; FIG. 7C shows partial Fourier transformation of the diffractive measurement; FIG. 7D shows amplitude reconstruction of the objects and FIG. 7E shows phase reconstruction of the objects; FIG. 8A shows the objects; FIG. 8B shows a diffraction measurement of the objects; FIG. 8C shows partial Fourier transformation of the measured intensity and FIG. 8D shows reconstructed image of the objects.

DETAILED DESCRIPTION OF EMBODIMENTS

The present invention provides a system and method for use in reconstruction of phase information based on input data indicative of diffractive measurements. As noted above, such diffractive measurements may be obtained by Coherent Diffractive Imaging (CDI) and/or lensless imaging techniques. It should however be noted that the diffractive patterns may be associated with forward scattering (i.e. transmission of light) and/or backward scattering (i.e. reflection).

Figure 1A:
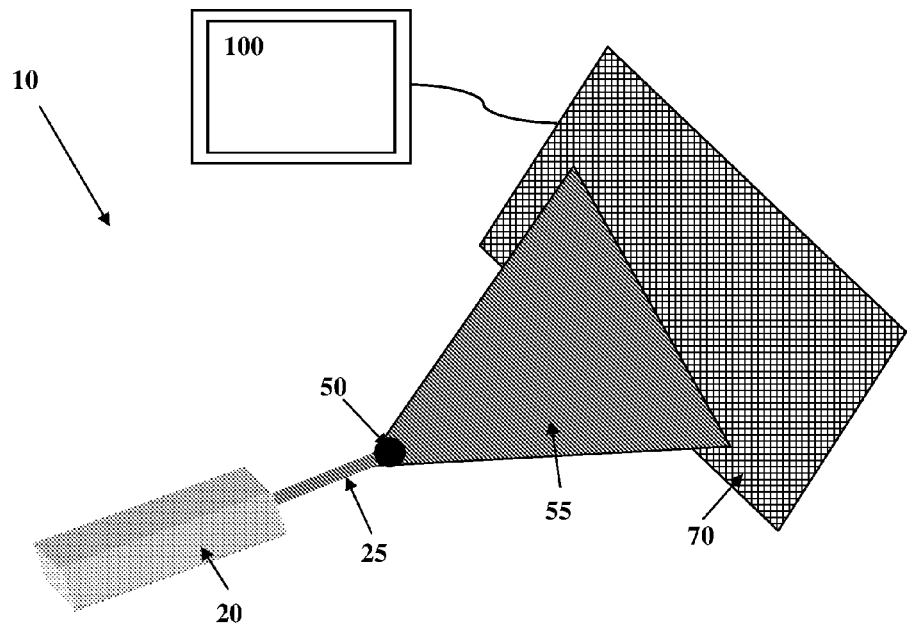
FIGS. 1A to 1C illustrate examples of an optical system for Coherent Diffractive Imaging (CDI) suitable for data acquisition for the technique of the present invention.

According to some embodiments, the input data may include at least three diffractive patterns such that first and second patterns are independent of one another as will be described below, and the third diffractive pattern includes an interference of the first and second diffractive patterns. In this connection reference is made to FIGS. 1A to 1C exemplifying an optical system 10 for lensless imaging of one or more objects 50.

The system includes a light source system 20 configured to provide coherent illumination of the object, and a detector 70 (e.g. pixel array) configured to collect light scattered from the object 50. The detector 70 may generally be connectable to a computerized system (e.g. system 100 for phase reconstruction according to the present invention) for collecting and processing the data. The optical system 10 may generally include additional elements which are not specifically shown here, such as a stand for the inspected object 50, various beam splitters for additional measurements, certain optical elements for directing light onto the sample etc.

It should be noted that the concept and details of lensless imaging or Coherent Diffractive Imaging (CDI) is generally well known in the art and thus will not be described herein in details but to note that lensless imaging utilizes light diffraction from the inspected object to collect information about parameters of the object such as structure and/or shape. The light source 20 (typically a laser light source) produces coherent light beam 25 and directs it towards the object 50. The light beam 25 impinges on the object 50 and is scattered to various directions, e.g. scattered light 55, such that at least some of the scattered light is collected at the far field by the detector 70. The detector 70 is typically a pixel array enabling detection of spatial distribution of the scattered light. It should be noted that the system 10 may be configured to collect back-scattered or forward-scattered radiation and the location of the detector 70 is to be determined accordingly.

At the far field, the scattered light is distributed as Fourier transform of the object. However, a typical detector 70 can provide only intensity information on the collected light, rather than the desired amplitude and phase information. Therefore, in order to reconstruct an image of the inspected object 50, the phase of the collected light should be recovered to enable calculation of inverse Fourier transform and reconstruct the object. Thus, the present invention provides a technique for use in reconstructing of the image data based on diffractive patterns collected by the detector 70 in imaging methods such as CDI.

As indicated above, the technique of the present invention utilizes input data indicative of acquired diffractive pattern. According to some embodiments, the input data includes at least three diffractive patterns collected by lensless imaging (or CDI) of an object to be inspected. Each of the collected diffractive patterns being a two-dimensional map indicating intensity distribution of scattered light as measured by a detector unit (e.g. detector 70). The input data, preferably including the at least three diffractive patterns, is being processed to reconstruct phase data for different rows (or columns) of the diffractive patterns resulting in a set of one-dimensional reconstructed vectors. After reconstruction of phase data for all of the rows (or columns) is complete, the set of one-dimensional reconstructed vectors is tailored together to form a complete two-dimensional map of reconstructed phase information. Based on the reconstructed phase information, inverse Fourier transform of the diffractive image data may be calculated to receive data about the object.

Figure 1B:
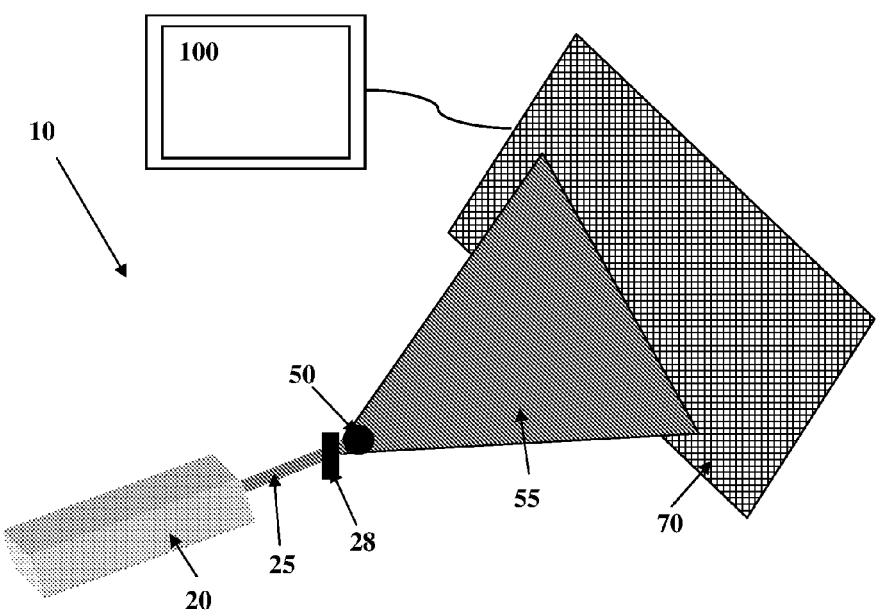

FIG. 1B illustrates an example of the optical system 10 suitable for using with the technique of the present invention for lensless imaging of an object 50. As shown in the figure, the detector 70 may be connected to a system for phase reconstruction of 2D images 100 according to the present invention. However, it should be noted that the data collected by the detector may be stored in a local or remote storage utility and later processed by the system of the present invention. The example of FIG. 1B is almost similar to the optical system of FIG. 1A but includes a controllable aperture 28 (in FIG. 1B) configured to enable collection of first and second independent diffractive patterns being indicative of part of the object 50. It should however be noted that the diffractive patterns may be collected utilizing a first and second illumination channels based on two different light sources and or collected using two separate but similar samples, e.g. two molecules. The third measurement providing the third diffraction pattern may include illumination of both parts of the sample (in case the two independent measurements are associated with parts of the sample) and/or the use of the two illumination channels used, and/or illumination of the two replicas of the sample together (e.g. one replica on the left and one on the right). It should be noted that the geometrical resolution of the detector 70 defines a maximal resolution possible in the reconstruction of the image data. As will be described below, the geometrical resolution of the detector 70 may be defined as $N_{kx}, N_{ky}$ describing the number of pixels in each row and column respectively.

Figure 1C:
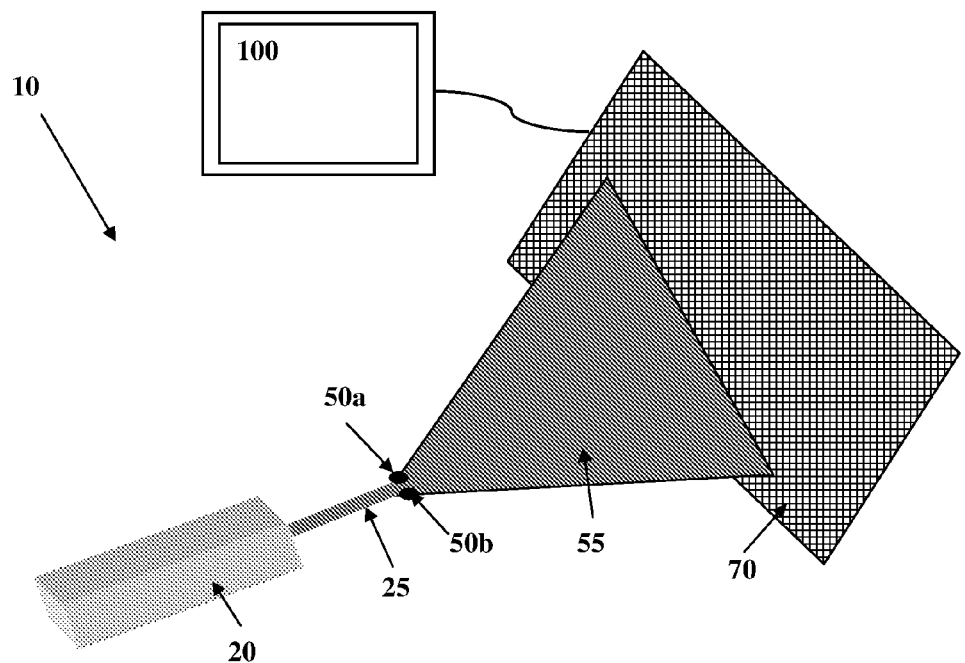

FIG. 1C illustrates one other example of the optical system 10 suitable for using with the technique of the present invention for lensless imaging. In this example, the system is configured for lensless imaging of two or more objects in a single shot (two such objects are shown 50a and 50b). According to some embodiments of the invention, a diffraction response from two or more objects being separated between them a distance l. The two or more objects, 50a and 50b in this non-limiting example, are of finite sizes that is preferably smaller than the distance l between them. The single-shot diffractive measurement is capable of providing accurate imaging of biological samples even under X-ray or electron scattering, which may generally destroy the sample and thus cannot be used for repetitive imaging. Thus, as will be described further below, the present technique may be used for phase reconstruction of a single-shot diffractive pattern generated from two or more well separated objects.

Figure 2A:
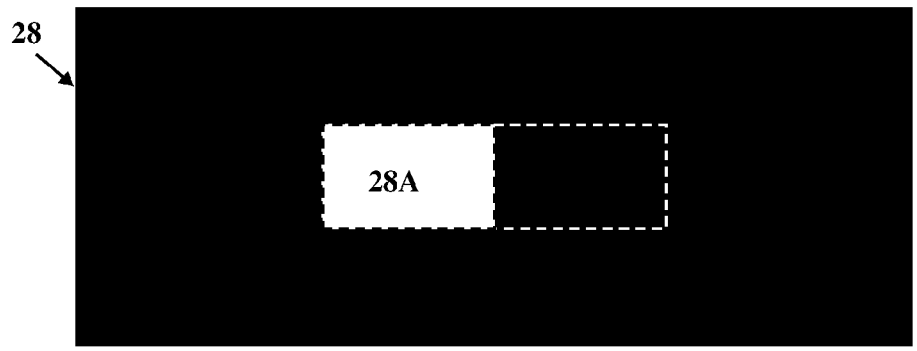
FIGS. 2A to 2C exemplify the use of a controllable aperture for data acquisition suitable for use with the technique of the present invention.
Figure 2B:
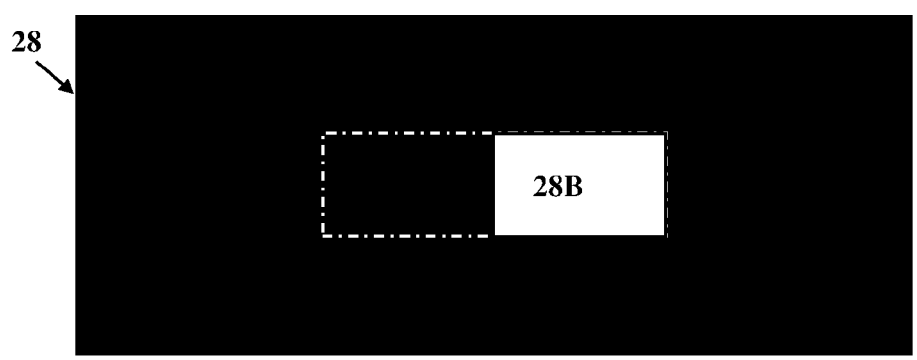
Figure 2C:
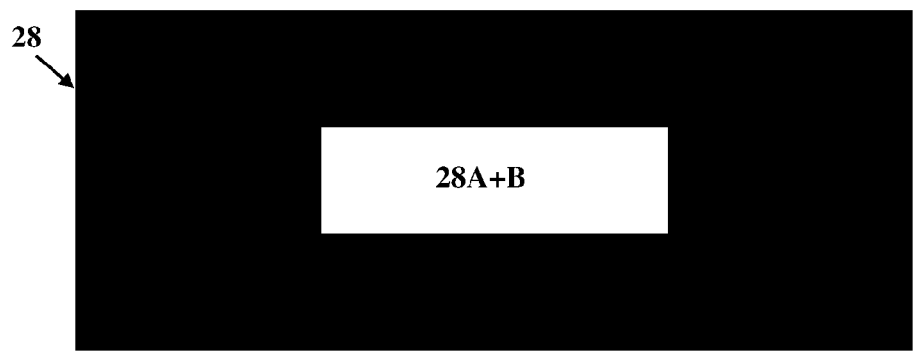

As noted, the at least three measurements include a first measurement using a first illumination configuration, a second measurement using a second illumination configuration, and a third measurement using a combined illumination configuration. In some embodiments as described in FIG. 1C, the at least three measurements correspond to diffractive patterns which may be extracted from the measured diffractive data as will be described further below, thus providing sufficient data from phase reconstruction in a single shot scattering measurement. This is while according to some other embodiments as described in FIGS. 1A and 1B, the illumination configurations correspond to the use of additional illumination channel, and/or illumination of part of the object 50 (as exemplified in FIG. 1B) and/or measurements of two replicas of the object. FIGS. 2A to 2C illustrate an example of the three configurations of the controllable aperture 28 shown in FIG. 1B. Generally, in order to provide sufficiently independent measurements, the controllable aperture is preferably located at a conjugated optical plane with respect to the sample, i.e. attached to the sample or in very close proximity thereto, or in an optical plane corresponding to image-object planes. As shown, a first illumination pattern includes light passage through one half 28A of the aperture, the second illumination pattern includes light passage through a second half 28B of the aperture and the third illumination pattern includes light passage through both parts of the aperture 28A+B.

According to some embodiments of the present invention, system 100 for phase reconstruction of 2D images 100 may be connectable to the one or more light sources and/or the controllable aperture 28 to provide control commands for opening or closing the corresponding illumination channels. Additionally, the system 100 may include a control unit configured to generate such control commands to thereby generate the required data indicative of diffractive patterns.

It should be noted that in order to enhance understanding and to simplify notations in the following description, the three measurements will be referred to herein below as $I_1=|E_1|^2$ for a first measurement, $I_2=|E_2|^2$ for a second measurement and $I_3=|E_1+E_2|^2$ for the third measurement. As indicated above, the third measurement may preferably be a combined measurement where the measured diffractive pattern includes interference of the two illumination configurations. It should also be noted that these notations apply for variation of optical path as well as to illuminating parts of the object or blocking a portion of the light as shown in FIG. 1B, or to illumination of two replicas of a similar object, and is generally used regardless of the actual measurement technique used. More specifically, the intensity fields of the first and second independent measurements are referred to as $I_1$ and $I_2$ and the intensity field of the third measurement is referred to as $I_3$.

Figure 3:
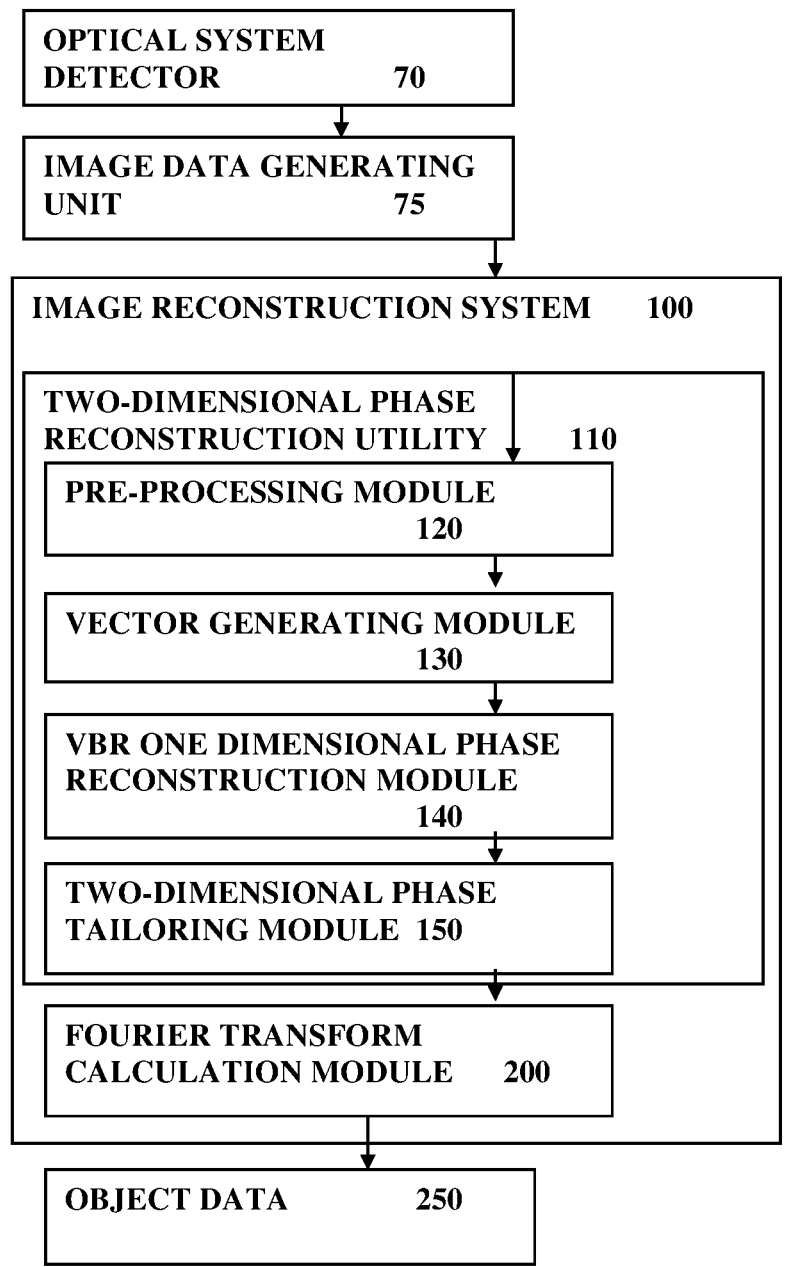
FIG. 3 illustrates a system for use in phase reconstruction based on data indicative of diffractive patterns according to some embodiments of the present invention.

Thus, the technique of the present invention provides for phase reconstruction of input data indicative of diffractive patterns of wave scattered from a sample to be inspected. In this connection reference is made to FIG. 3 illustrating a system for reconstruction of two-dimensional phase 100 in the form of a block diagram. The system 100 is generally a computerized system including one or more data processing utilities, storage utility and suitable input and output utilities. The main processing utility includes a two-dimensional phase reconstruction utility 110 according to the present invention, and may also include an inverse Fourier transform calculation module 200 configured to use the reconstructed phase information to obtain data about the inspected object. Generally, the system 100 receives input data indicative of at least three diffractive measurements as indicated above from a detector unit 70 and a corresponding image data generating unit 75 associated with the optical setup for inspection. It should however be noted that the data may be received from any type of storing utility or communication utility, in accordance with prior measurement.

The two-dimensional phase reconstruction utility 110 may generally include various computational modules for phase reconstruction. As shown in FIG. 3, the 2D phase reconstruction utility 110 includes a pre-processing module 120, a vector generating module (VGM) 130, a one-dimensional vectorial phase retrieval module (VPR) 140 and a two-dimensional phase tailoring module (2DPT) 150. The pre-processing module 120 is generally configured and operable to determine if the input data is appropriate for phase reconstruction and/or contains operation commands for the system. Additionally, the pre-processing module 120 may operate to calculate required intermediate data based on input data indicative of measurements $I_1$, $I_2$ and $I_3$, the intermediate data is generally associated with relative phase between measurements of two different illumination channels as described above. After verification and intermediate calculation, the pre-processing module 120 transmits the data to be calculated to the vector generating module 130 (VGM) which operates to separate the input data to plurality of one-dimensional vectors to enable individual processing of each of the 1D vectors. The VGM 130 actually operates to shift the phase reconstruction problem form a single two-dimensional problem into a set of one-dimensional phase problems, where each of the 1D vectors corresponds to a line (or a column) of the original 2D diffractive patterns. The VGM 130 then operates to transmit vector data corresponding to each line/column of the input data (indicative of three 2D diffractive patterns) to the one-dimensional vectorial phase retrieval module (VPR) 140 for performing 1D phase reconstruction. Generally the VPR module 140 may utilize any known phase reconstruction technique capable of calculating phase information based on one-dimensional data, for example the VPR module 140 may utilize Vectorial Phase Retrieval (VPR) technique developed by the inventors of the present invention which will be described in more details below.

After the VPR module 140 successfully reconstructs the phase for each of the 1D vectors, the reconstructed phase vectors as well as the input data are transmitted to the two-dimensional phase tailoring module (2DPT) 150 for tailoring back to two-dimensional diffractive pattern with the reconstructed phase information. The resulting diffractive pattern including the reconstructed phase information may be stored or transferred for further analysis and/or transmitted to the Fourier transform calculation module 200 which may operate to calculate inverse Fourier transform of the diffractive pattern to provide data about the structure of the object.

Generally, the image reconstruction system 100 may provide output in the form of object data 250 being indicative of image data of the sample object. However, according to some embodiments the image reconstruction system 100 may output data indicative of the diffractive measurements including reconstructed phase information to thereby enable calculation of inverse Fourier transform by a separate system of analysis of the Fourier data of the sample.

Figure 4:
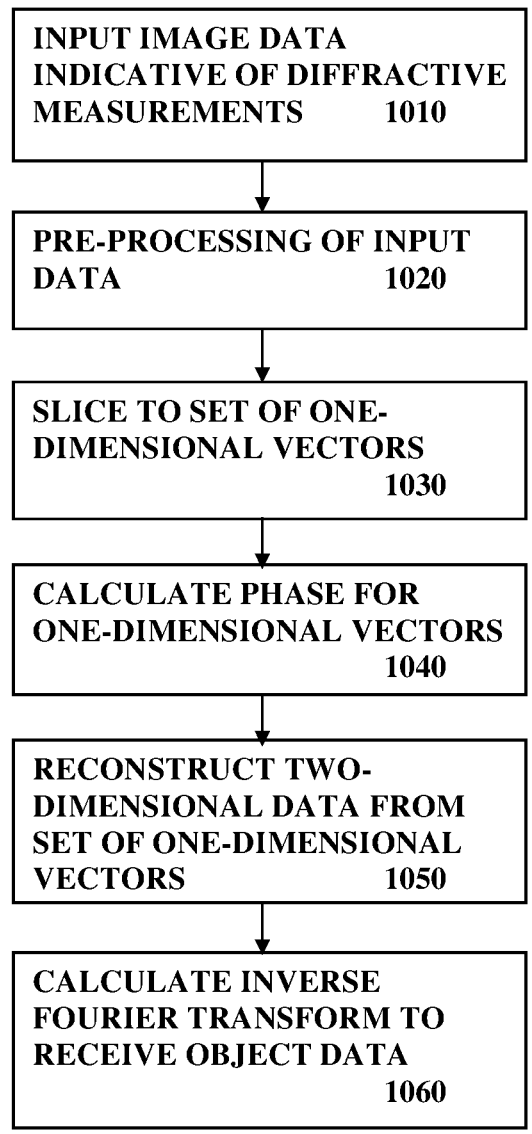
FIG. 4 illustrates an example of the technique of the present invention in a way of a block diagram.

Reference is made to FIG. 4 illustrating a flow chart exemplifying the technique of the present invention as used in phase reconstruction of two-dimensional objects. As shown, the technique utilizes input data (step 1010) including data indicative of the diffractive measurements. Such input data may also include meta data such as data about geometrical resolution in which the diffractive measurements were taken. The input data may generally undergo pre-processing (step 1020) to identify errors in the data or control commands and possibly to provide intermediate data such as relative phase data, which will be described further below. After pre-processing of the input data, the at least three diffractive measurements are separated to slices, i.e. each two-dimensional data matrix is divided to plurality of one-dimensional vectors, lines or columns of the matrix (step 1030). The one-dimensional vectors thus include sets of three (generally at least three) vectors of a certain line/column, one of each of the diffractive measurements. Each of these sets is then processed together (step 1040) using Vectorial Phase Retrieval (VPR) technique developed by the inventors of the present invention. This processing phase provides phase reconstruction for a plurality of one-dimensional vectors, while each includes certain linear phase ambiguity. These plurality of vectors are tailored together by identifying the correct linear phase for each of the vectors to provide two-dimensional diffractive measurement data with reconstructed phase information (step 1050). After phase reconstruction is complete, an inverse Fourier transform of the diffractive measurement data can be calculated (step 1060) to provide object's data. It should be noted that the system 100 of FIG. 3 may be any type of computerized system configured and operable to perform the calculation steps as described in FIG. 4.

Figure 5:
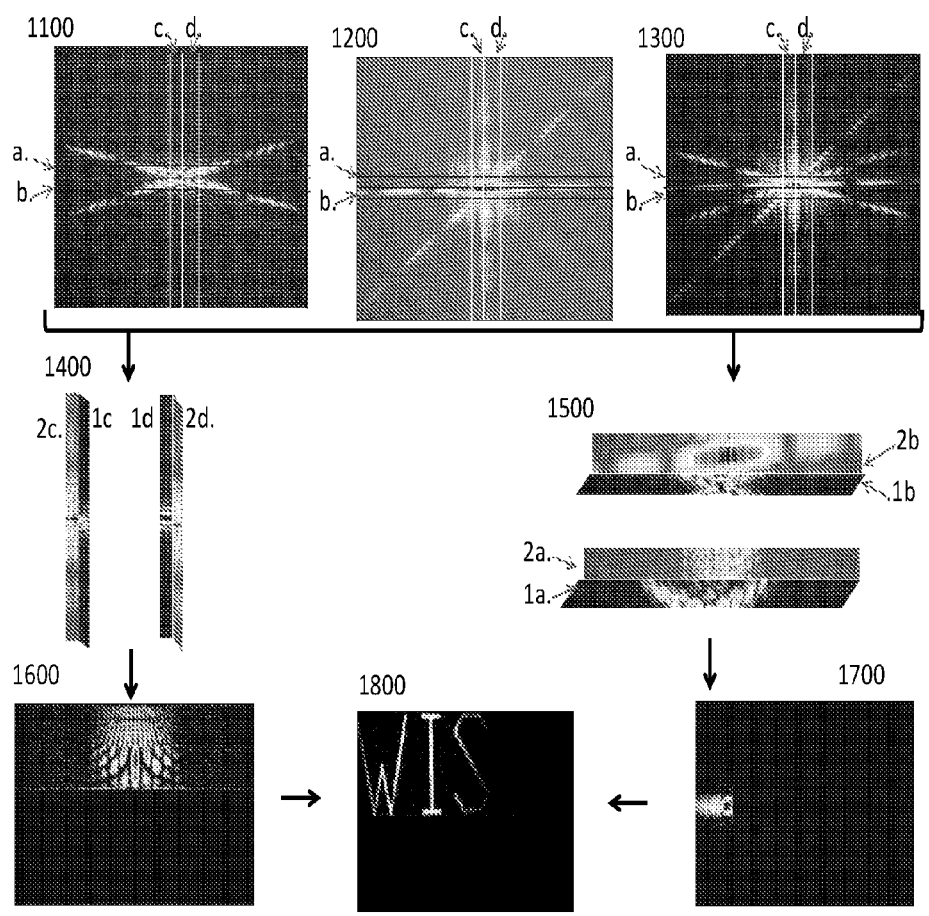
FIG. 5 exemplifies the technique of the present invention for phase reconstruction.

The phase reconstruction technique of the present invention is exemplified in FIG. 5 illustrating collected diffractive patterns 1100, 1200 and 1300, one dimensional slices of the patterns used for vectorial phase reconstruction 1400 and 1500, semi-reconstructed phase maps 1600 and 1700 and fully reconstructed image data 1800. The three diffractive patterns 1100, 1200 and 1300 may be collected as described above, such that two patterns are independent and the third is an interference of the first and second, and are provided as input data. The technique may then operate along either the horizontal or vertical routes, where the input diffractive patterns are sliced to generate sets of one-dimensional vectors 1400 for the vertical route or 1500 for the horizontal route and are used to determine the phase data along each slice. It should be noted that in order to simplify the figure, only two slices are shown here, the present technique however utilizes corresponding slices from all of the diffractive patterns provided in the input data, and preferably utilizes the relative phase map rather than interference diffractive pattern. The phase information is used to determine semi reconstructed patterns 1600 or 1700, where the input data is Fourier transformed along the selected vertical or horizontal axis. The phase shifts of each row or column may then be determined to tailor the slices together and provide the fully reconstructed image data 1800. It should be noted that the technique may utilize any one of the horizontal or vertical paths to determine the reconstructed phase information and provide the corresponding image data.

As indicated above, the technique of the present invention enables 2D phase reconstruction of diffractive measurements. According to some embodiments the technique utilizes input data including three diffractive measurements/patterns such as $I_1$, $I_2$ and $I_3$ acquired as described above with reference to FIGS. 1A and 1B. As also indicated above, the diffractive measurements correspond to intensity of light fields provided by varying the illumination channel and can be described as follows:

$$I_{1,2} = |\tilde{E}_{1,2}(\vec{k})|^2, I_3 = |\tilde{E}_3(\vec{k})|^2 = |\tilde{E}_1(\vec{k}) + \tilde{E}_2(\vec{k})|^2 \quad \text{(equation 1)}$$

where $\vec{k} = (k_x, k_y)$ is a spatial frequency vector, i.e. Fourier component of the object, and generally corresponds to certain pixel of the detector. As indicated above, the geometrical resolution of the detector $N_{kx}, N_{ky}$ limits the maximal resolution achievable by reconstruction (as dictated by the Nyquist theorem). The technique of the present invention may require certain over-sampling such that maximal resolution achievable for the reconstructed image data may be $n_x, n_y$, while $N_{kx} = 4n_x$ and $N_{ky} = 2n_y$.

The input data may be pre-processed by pre-processing module 120 to calculate intermediate data in the form of a cross term indicative of a relative phase between the two optical fields $E_1$ and $E_2$, i.e. to calculate the term $\tilde{E}_1(\vec{k}) \tilde{E}_2^*(\vec{k})$. For example the pre-processing module may perform calculation as follows:

$$\Re e[\tilde{E}_1(\vec{k}) \tilde{E}_2^*(\vec{k})] = \frac{1}{2}[|\tilde{E}_3(\vec{k})|^2 - |\tilde{E}_1(\vec{k})|^2 - |\tilde{E}_2(\vec{k})|^2] \quad \text{(equation 2)}$$

$$R(x, k_y) = \mathcal{F}_x^{-1}(\Re e[\tilde{E}_1(\vec{k}) \tilde{E}_2^*(\vec{k})]) \quad \text{(equation 3)}$$

$$I(x, k_y) = \begin{cases} iR(x, k_y) & x \leq 2n_x = \frac{1}{2} N_{kx} \\ (iR(4n_x - x, k_y))^* & x > 2n_x = \frac{1}{2} N_{kx} \end{cases} \quad \text{(equation 4)}$$

$$\tilde{E}_1(\vec{k}) \tilde{E}_2^*(\vec{k}) = \mathcal{F}_x[R(x, k_y) + iI(x, k_y)] \quad \text{(equation 5)}$$

where $\Re e$ indicates that equation 1 calculates the real part of the interference term; $R(x, k_y)$ and $I(x, k_y)$ are respectively real and imaginary parts corresponding to intermediate calculations; $\mathcal{F}_x$ and $\mathcal{F}_x^{-1}$ are one-dimensional Fourier and inverse Fourier operators along the x axis, i is the imaginary unit (i.e. $i^2 = -1$) and $k_{x,y}$ stand for coordinates (pixels) in the detector plane and x,y stand for coordinates (pixels) of the reconstructed image data. As noted above the input data may generally be in the form of three matrices each having $4n_x$ by $2n_y$ pixels.

With the relative phase term calculated, the input data including data pieces indicative of the first and second diffractive patterns, together with data about the relative phase is transmitted to the Vector Generating Module (VGM) 130. The VGM 130 is configured and operable to generate a set of one-dimensional vectors, each corresponding to a line of the detected intensity field (and the associated line of the intermediate term). The VGM transmits the one-dimensional vectors to the VPR one dimensional phase reconstruction module 140 for line-by-line phase reconstruction. The 1D vectors may generally include the following terms:

$$|\tilde{E}_1(k_x, k_y = m)|^2, |\tilde{E}_2(k_x, k_y = m)|^2, \text{ and } \tilde{E}_1(k_x, k_y = m) \tilde{E}_2^*(k_x, k_y = m)$$

The VPR module 140 is configured and operable for phase reconstruction of one-dimensional input data based on at least three vectors corresponding to first and second independent measurements and a third measurement being indicative of interferences between the first and second measurements. The VPR module operates to reconstruct the phase information up to an ambiguous linear phase for each of set of at least three 1D vectors. Thus, the VPR module calculates the unknown phases $X_{1,2}(k)$ defined by $E_{1,2}(\vec{k}) = |E_{1,2}(\vec{k})| X_{1,2}(\vec{k})$ for $\vec{k} = (k_x, k_y = m)$.

More specifically, for each set of 1D input vectors, the VPR module 140 may operate to determine the reconstructed phase data utilizing matrix calculations. For example, the VPR module 140 may utilize a matrix $A_m$ of size $8n_x \times 8n_x$ (i.e. $2N_{kx} \times 2N_{kx}$) of the form:

$$(A_m)_{k,l} = \quad \text{(equation 6)}$$

$$\begin{cases} |E_1(l, m)| e^{i \frac{l(k+2n_x)2\pi}{4n_x}} & k \leq 2n_x, \\ & l \leq 2n_x \\ |E_2(l - 2n_x, m)| e^{i \frac{l(k+2n_x)2\pi}{4n_x}} & 4n_x \geq k > 2n_x, \\ & 4n_x \geq k > 2n_x \\ E_1(l - 4n_x, m) E_2^*(l - 2n_x, m) & l > 4n_x, k = l - 4n_x \\ |E_1(l - 4n_x, m)| |E_2(l - 4n_x, m)| & l > 4n_x, k = l \\ 0 & \text{otherwise} \end{cases}$$

and may operate to recover the unknown phases $X_{1,2}(k_x, k_y = m)$ by solving a linear problem of the form $$A_m X_m = 0 \quad \text{(equation 7)}$$

where $X_m=[X_1(k_x,k_y=m), X_2(k_x,k_y=m)]$ is a 1D vector of length $8n_x$ (i.e. $2N_{kx}$).

When the VPR module 140 completes the phase reconstruction of all of the sets of 1D vectors, it provides corresponding sets of 1D phase-vectors each corresponding to phase information (up to an unknown linear phase) of each row of the input data. The set of phase-vectors is then transmitted to the Two-Dimensional Phase Tailoring Module (TDPT module) 150 which is configured and operable to combine all of the phase-vectors into a matrix of two-dimensional phase data.

To this end the TDPT module 150 is configured to determine a phase shift associated with each of the 1D phase-vectors determined by the VPR module to thereby combine the phase shifts to reconstruct phase variations along the perpendicular axis.

Generally, the TDPT module 150 may utilize knowledge of the illumination channel and/or aperture providing illumination of the object, i.e. known support of reconstructed data. This may be determined by solution of a set of linear equations of the form:

$$\Sigma_m |E_{1,2}(k_x,m)| X_{1,2}(m) \xi(m) e^{imy} = 0 \qquad \text{(equation 8)}$$

for all values of y outside the illumination region of the illumination channel/aperture. Here $\xi(m)$ is the phase shift of the corresponding 1D phase-vector $X_{1,2}(k_x,m)$ and the summation is over all values of $m=k_y$. It should be noted that equation 8 can be presented as $M\xi=0$ thereby enabling to determine the phase shift by solving the linear problem.

It should be noted that although objects of finite size are defined as having a compact support, a typical object being inspected may be of unknown size and thus the support may be unknown. In such cases where the support size is unknown, the technique of the present invention may utilize scanning the possible supports size to determine the phase vectors $X_m$ and $\xi(m)$. If the assumed support size is too small/large, the determined phase vector will be incompatible with the required image data providing phase residue outside of the assumed support. To this end the system may include a support estimation module being configured to provide estimation of the support size to the VPR module 140 and the TDPT module 150 and to analyze the determined phase vector with respect to the determined inverse Fourier transform of the diffractive data (being one- or two-dimensional). The support estimation module can thus determine the correct support size in accordance with the phase residue such that minimal phase residue indicates that the corresponding assumed support size is correct. It should be noted that the support size is generally determined separately for the VPR module 140 and the TDPT module 150 to thereby provide independent support size along the vertical and horizontal axes of the object 50.

In practice, determining a solution for equations 7 and 8 may be done by selecting a column of the matrix (being $A_m$ or M) having maximal norm, removing the index corresponding to the selected column from the associated vector (X or $\xi$), and minimizing the difference between the remaining part of the matrix multiplied by the remaining part of the vector and the selected vector. For example, to determine the vector $\xi$ which minimizes the expression:

$$\|M\_\xi\_ - M_1\|^2 \qquad \text{(equation 9)}$$

where $M_1$ is the selected column having maximal norm, $M\_$ is the remaining matrix without the selected column, and $\xi\_$ is the remaining vector without the index corresponding to the selected column. It should also be noted that the support size may be determined (if unknown), utilizing the minimizer $\xi\_$ indicated in equation 9. As indicated above, for incorrect support size, the minimizer $\xi\_$ after being normalized to provide phase data may generate a phase residue outside the assumed support size. Thus the corresponding modules may utilize various assumed support sizes to minimize the phase residue and thus determine the correct size of the object 50.

Figure 6A:
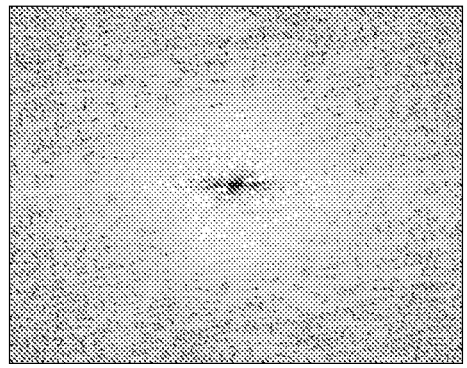
FIGS. 6A-6E show three corresponding diffractive patterns provided as input data (FIGS. 6A-6C) and image data for the reconstructed and original images respectively (FIGS. 6D-6E)
Figure 6B:
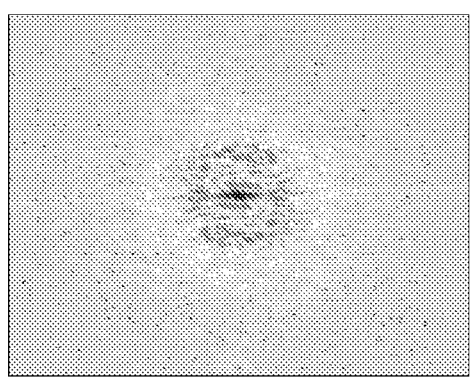
Figure 6C:
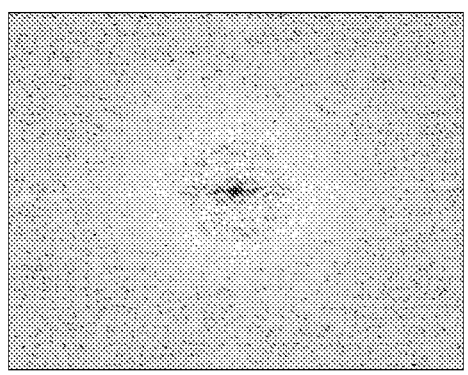
Figure 6D:
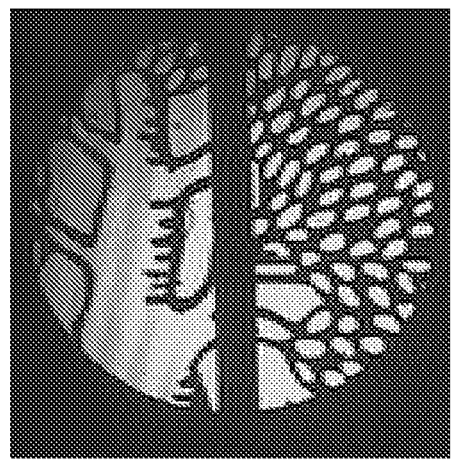
Figure 6E:
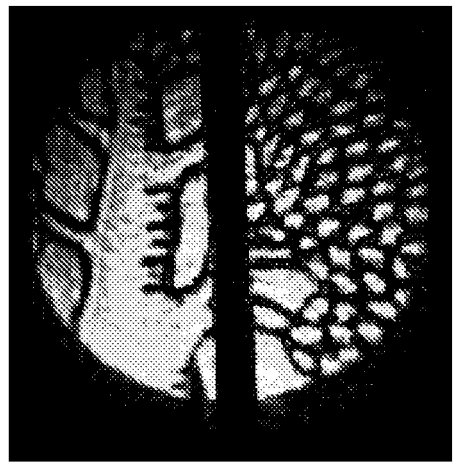

Reference is made to FIGS. 6A-6E showing an additional set of input and reconstructed data provided by the technique of the invention. FIGS. 6A-6C show respectively diffractive patterns as collected from an object with a first illumination channel, second illumination channel and a combined channel as described above. The input data have been processed in accordance with the present invention as described above to reconstruct image data indicative of the object. FIG. 6D shows the reconstructed image data determined by the technique of the present invention. The reconstructed image data can be compared to the original image shown in FIG. 6E.

Additionally, as indicated above, with reference to FIG. 1C, the technique of the present invention may also be used for phase reconstruction based on a single-shot diffractive measurement of two or more objects. FIGS. 7A-7E and 8A-8D show phase reconstruction of a single shot of two (FIGS. 7A-7E) and three (FIGS. 8A-8D) objects according to the present technique.

The phase reconstruction of a single-shot diffractive measurement takes advantage of the inventors' understanding that the Fourier transform of the diffractive intensity pattern is indicative of the autocorrelation of the imaged object. When two or more spatially separated objects are being imaged simultaneously, the inverse Fourier transform of the diffractive pattern includes the sum of the objects autocorrelations a spatially distinct cross-correlation of them. This allows for extraction of the required information $|\tilde{E}_1(k_x,k_y=m)|^2$, $|\tilde{E}_2(k_x,k_y=m)|^2$, and $\tilde{E}_1(k_x,k_y=m)\tilde{E}_2^*(k_x,k_y=m)$ corresponding to individual object diffractive response and interference relation between the objects as described above.

In this connection, denoting the two objects $A(\vec{x})$, $B(\vec{x})$ (and possibly $C(\vec{x})$ when three objects are used, and so on for more objects) and their corresponding spectra (Fourier transform/diffractive response) as $\tilde{A}(\vec{k})$, $\tilde{B}(\vec{k})$, the diffractive response of both objects being separated a distance l is:

$$F[A(\vec{x})+B(\vec{x}+\vec{l})]=\tilde{A}(\vec{k})+\tilde{B}(\vec{k})\cdot e^{i\vec{l}\vec{k}} \qquad \text{(equation 10)}$$

where F stands for the Fourier transform.

Figure 7A:
FIG. 7A-7E show experimental results of a single-shot phase reconstruction according to embodiments of the present invention.
Figure 7B:
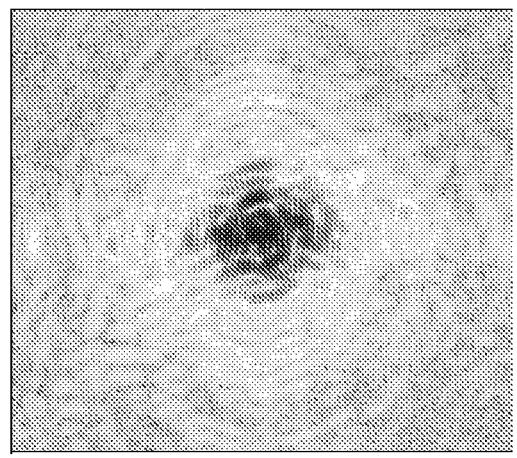
Figure 7C:
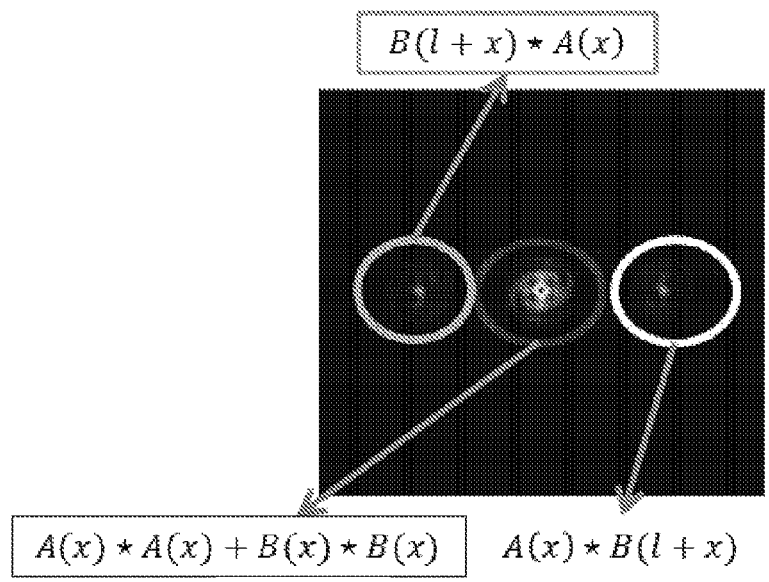
Figure 7D:
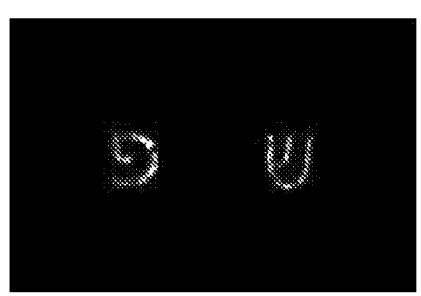
Figure 7E:
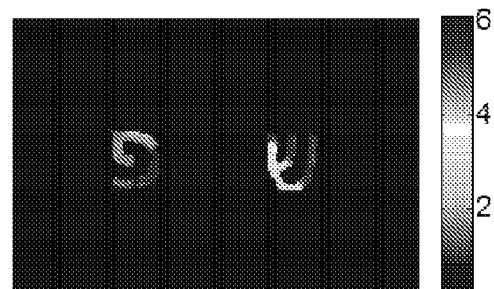
Figure 8A:
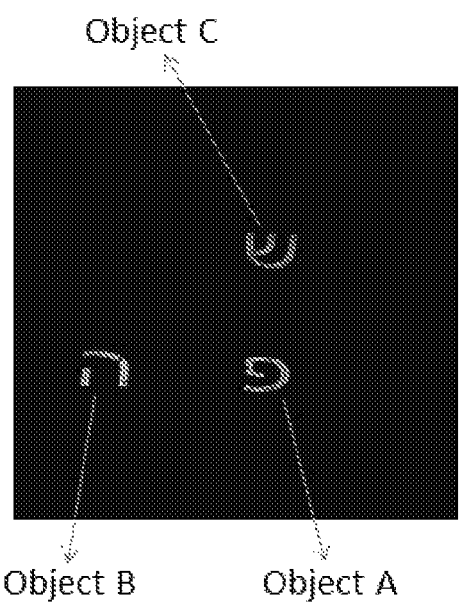
FIGS. 8A-8D show experimental results of a single-shot phase reconstruction of three objects according to embodiments of the present invention
Figure 8B:
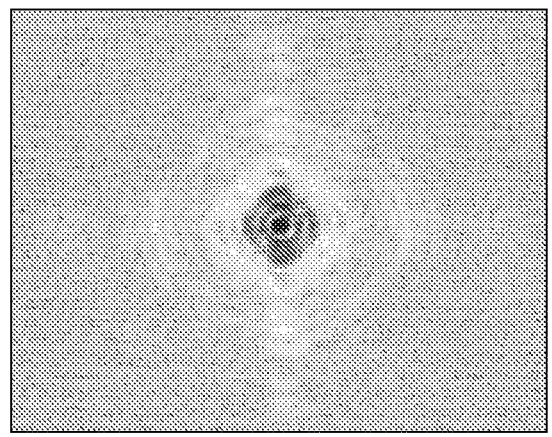
Figure 8C:
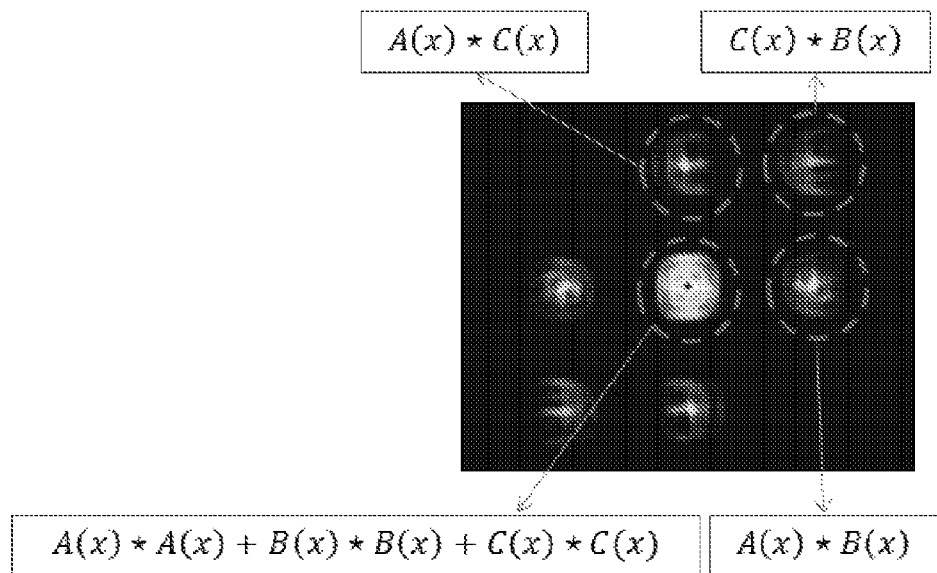
Figure 8D:
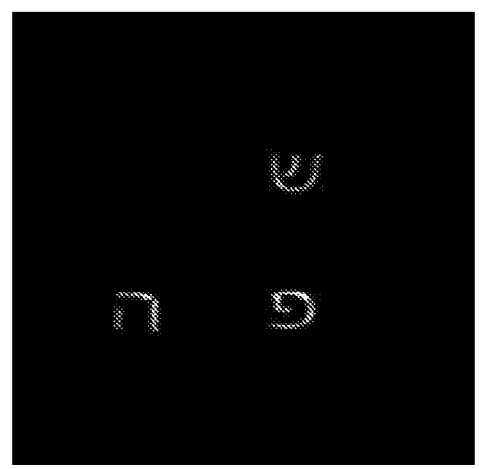

The actual measurement provides only the intensity information thus requiring the phase reconstruction. However, the inverse Fourier transform of the measured intensity of the diffractive pattern can be expressed in terms of single object auto-correlation and cross-correlation between the objects:

$$IF[|\tilde{A}(\vec{k})+\tilde{B}(\vec{k})\cdot e^{i\vec{l}\vec{k}}|^2]=A(\vec{x})\star A(\vec{x})+B(\vec{x})\star B(\vec{x})++A(\vec{x})\star B(\vec{x}+\vec{l})+B(\vec{x}+\vec{l})\star A(\vec{x}) \qquad \text{(equation 11)}$$

here $\star$ is the 2D cross-correlation operator, i.e. $f\star g(\vec{d})=\int f^*(\vec{x})g(\vec{x}+\vec{d})d\vec{x}$, where $f^*$ denoted the complex conjugate of f. As the two or more objects are finite, i.e. $A(\vec{x})$ and $B(\vec{x})$ have limited (compact) support, and the distance between them l is larger than the size of the objects, the cross correlation terms are separated from the autocorrelation terms as shown in FIG. 7C. This allows separation between the cross correlation and auto-correlation terms to determine the required intensity patterns. A Fourier transform of the auto-correlation term of the two objects provides:

$$F[A(\vec{x}) \star A(\vec{x}) + B(\vec{x}) \star B(\vec{x})] = |\tilde{A}(\vec{k})|^2 + |\tilde{B}(\vec{k})|^2 \quad \text{(equation 12)}$$

This is while Fourier transforms of the different cross-correlation terms provide:

$$F[A(\vec{x}) \star B(\vec{x}+\vec{l})] = e^{-i\vec{l}\cdot\vec{k}} \tilde{A}^*(\vec{k}) \tilde{B}(\vec{k})$$

$$F[B(\vec{x}+\vec{l}) \star A(\vec{x})] = e^{i\vec{l}\cdot\vec{k}} \tilde{A}(\vec{k}) \tilde{B}^*(\vec{k}) \text{ and thus also}$$

$$(e^{-i\vec{l}\cdot\vec{k}} \tilde{A}(\vec{k}) \tilde{B}^*(\vec{k}))(e^{i\vec{l}\cdot\vec{k}} \tilde{A}^*(\vec{k}) \tilde{B}(\vec{k})) =$$
$$|\tilde{A}(\vec{k})|^2 |\tilde{B}(\vec{k})|^2 \quad \text{(equation 13)}$$

Equations 12 and 13 provide data on the sum and product of $|\tilde{A}(\vec{k})|^2$ and $|\tilde{B}(\vec{k})|^2$. Based on the sum and product of the intensities, the information about separate intensity data for $|\tilde{A}(\vec{k})|^2$ and $|\tilde{B}(\vec{k})|^2$ can be determined, but with certain ambiguity regarding which value corresponds to $|\tilde{A}(\vec{k})|^2$ and which to $|\tilde{B}(\vec{k})|^2$. To this end a difference value for each pixel (each k value) can be defined and utilizing continuity of the difference value, the problem may thus be converted to an associated sign problem, which can be solved by defining regions of similar sign and borders between them. Limitation of the number of equations for the sign problem may also utilize data about the compact support of the objects, i.e. Fourier transform of the difference values is zero outside of the compact support regions.

It should be noted that the naïve solution to the sign problem would require that the Fourier transform of $|\text{Diff}(\vec{k})|\text{Sign}(\vec{k})$ at any point $\vec{x}$ outside of the compact support of any of the objects is zero. This requirement has a-priory a higher number of unknowns with respect to the number of equations. However, the inventors' understanding provides for greatly reducing the number of unknowns. To this end, the sign between two neighboring points cannot change unless there is a zero between the points. Thus, to determine the sign value of Diff(k), the technique of the invention may utilize separation of Diff(k) into plurality of sign-regions, regions of similar sign separated by boundaries where the sign of Diff(k) is unknown. This technique may greatly reduce the number of unknowns in the sign problem, often by an order of magnitude, i.e. a factor of 10, or more.

Thus the information about finiteness of the two or more objects (compact support thereof) and the separation between them allows determination of the individual values of $|\tilde{A}(\vec{k})|^2$ and $|\tilde{B}(\vec{k})|^2$, from which, according to the description above, phase can be retrieved by the VPR method. As indicated above, the phase reconstruction technique utilizes information about individual diffractive response, i.e. $|\tilde{A}(\vec{k})|^2$ and $|\tilde{B}(\vec{k})|^2$, and data about interference relation between the objects (or as described above between the illumination paths), i.e. $\tilde{A}(\vec{k})\tilde{B}^*(\vec{k})$.

Thus, the present invention provides a novel technique for use in phase reconstruction of two-dimensional diffractive data. It should also be understood that the system according to the invention may be a suitably programmed computer. As indicated above, the technique may be implemented by a computerized system, or may be embedded therein, being configured to receive input data from a measurement system and/or a remote storage utility. Likewise, the invention contemplates a computer program being readable by a computer for executing the method of the invention. The invention further contemplates a machine-readable memory tangibly embodying a program of instructions executable by the machine for executing the method of the invention. Those skilled in the art will readily appreciate that various modifications and changes can be applied to the embodiments of the invention as hereinbefore described without departing from its scope defined in and by the appended claims.

The invention claimed is:

1. A method for use in reconstruction of phase information associated with a two-dimensional diffractive response of one or more objects, the method comprising:
   providing input data indicative of at least three intensity diffractive patterns associated with one or more diffractive responses from said one or more objects, such that first and second diffractive patterns are independent of one another and the third diffractive pattern includes an interference of the first and the second diffractive patterns;
   dividing each of at least said independent and interfering intensity diffractive patterns into plurality of one-dimensional slices to thereby form plurality of sets of matching slices thereof; and
   tailoring the one-dimensional phase data;
   reconstructed from said plurality of matching slices to thereby reconstruct a two-dimensional phase data associated with said diffractive responses, said tailoring of the reconstructed one-dimensional phase data comprising determining phase shifts associated with each of said one-dimensional slices, said reconstructed two-dimensional phase data suitable for reconstruction of image data.

2. The method of claim 1, wherein said one or more diffractive responses comprises diffractive responses of two or more objects, the method further comprising generating said input data based on said diffractive responses, said generating comprising determining cross-correlation and auto-correlation relations between said two or more objects from said diffractive responses to thereby determine intensity diffractive patterns of said objects and interference relations between said two or more objects.

3. The method of claim 1, wherein said at least three diffractive patterns are associated with diffractive response of the one or more objects to at least three illumination channels.

4. The method of claim 3, wherein said at least three diffractive patterns comprise data indicative of at least:
   a first diffractive pattern generated by a first coherent illumination;
   a second diffractive pattern generated by a second coherent illumination; and
   a third diffractive pattern generated by a combination of the first and second coherent illuminations.

5. The method of claim 4, wherein said determining reconstructed one-dimensional phase data for said plurality of one-dimensional slices comprising utilizing a cross term between said at least three diffractive patterns, said cross-term being indicative of a relative phase difference between the first and second diffractive patterns.

6. The method of claim 1, wherein said determining said reconstructed one-dimensional phase data for each of said plurality of one-dimensional slices comprises utilizing one-dimensional vectorial phase retrieval technique.

7. The method of claim 1,
   wherein said input data comprises a single-shot diffractive response of two or more of said objects; and wherein said method further comprises:

determining from said single-shot diffractive response, auto-correlation of said two or more objects and cross-correlation between them;
identifying intensity diffractive patterns of each of said two or more objects and interference relations between them.

8. A software product, embedded on a non-transitory computer readable medium and carrying computer readable code comprising instructions such that when operated on a computer system cause the computer system to execute method steps for use in reconstruction of phase information associated with a two-dimensional diffractive response of one or more objects, the steps comprising:
providing input data indicative of at least three intensity diffractive patterns associated with one or more diffractive responses from said one or more objects, such that first and second diffractive patterns are independent of one another and the third diffractive pattern includes an interference of the first and the second diffractive patterns;
dividing each of at least said independent and interfering intensity diffractive patterns into plurality of one-dimensional slices to thereby form plurality of sets of matching slices thereof; and
tailoring the one-dimensional phase data;
reconstructed from said plurality of matching slices to thereby reconstruct a two-dimensional phase data associated with said diffractive responses, said tailoring of the reconstructed one-dimensional phase data comprising determining phase shifts associated with each of said one-dimensional slices, said reconstructed two-dimensional phase data suitable for reconstruction of image data.

9. A system for use in phase reconstruction, the system comprising a processing utility configured for processing input data being indicative of at least three two-dimensional diffractive patterns associated with one or more diffractive responses of one or more objects, and to determine reconstructed phase data based on said input data; the processing utility comprising:
a vector generating module configured to receive said one or more diffractive responses and to generate a corresponding plurality of sets of one-dimensional vectors respectively corresponding to plurality of one-dimensional slices of said at least three two-dimensional diffractive patterns;
a one-dimensional phase reconstruction module configured to receive said sets of one-dimensional vectors, and to determine said reconstructed one-dimensional phase data associated with said sets of one-dimensional vectors; and a two-dimensional phase tailoring module configured to perform tailoring by receiving data indicative of reconstructed one-dimensional phase data from said one-dimensional phase reconstruction module and to generate corresponding said reconstructed two-dimensional phase data indicative of reconstructed phase information associated with said input data.

10. The system of claim 9, wherein the processing utility is configured and operable for reconstruction of phase information based on input data, said input data comprises said at least three diffractive patterns associated with said diffractive response of said one or more objects.

11. The system of claim 9, wherein said processing utility comprises a pre-processing module configured and operable to receive and process said input data to generate data indicative of a relative phase difference between at least two diffractive patterns of said one or more two-dimensional diffractive responses.

12. The system of claim 9, wherein the processing utility comprises a pre-processing module configured and operable to receive and process data indicative of at least one diffractive pattern associated with a diffraction response of two or more objects, said pre-processing module being configured to determine input data based on said data indicative of at least one diffractive pattern, said input data comprising diffraction pattern of each of said at least two objects and an interference relation between them.

13. The system of claim 9 configured for lens-less imaging, the system further comprising:
at least first and second illumination channels for illuminating an object to be inspected,
a detector unit comprising a pixel array for detecting scattered radiation from the object, and
a control unit configured and operable for receiving data indicative of detected scattered radiation from said detector unit and processing said data to determine reconstructed image data of said object; said control unit being configured and operable for receiving said input data being indicative of scattered light caused by the first and second illumination channels and for processing said input data to reconstruct image data indicative of the object to be inspected;
said processing comprising determining an inverse Fourier transform based on the two-dimensional reconstructed phase data and said detected diffractive patterns to thereby reconstruct image data of the object.

14. The system of claim 13, wherein the control unit being configured and operable to collect input data comprising first second and third diffractive patterns respectively associated with the first, second illumination channels and interference thereof.

* * * * *